United States Patent
Daniel et al.

(10) Patent No.: US 7,947,746 B2
(45) Date of Patent: May 24, 2011

(54) PROCESS FOR THE CONVERSION OF HYDROCARBONS INTO ETHANOL

(75) Inventors: Berian John Daniel, Beverley (GB); Benjamin Patrick Gracey, Hull (GB); John Glenn Sunley, Cottingham (GB)

(73) Assignee: BP P.L.C., London (GB)

( * ) Notice: Subject to any disclaimer, the term of this patent is extended or adjusted under 35 U.S.C. 154(b) by 0 days.

(21) Appl. No.: 12/735,094

(22) PCT Filed: Dec. 12, 2008

(86) PCT No.: PCT/GB2008/004095
§ 371 (c)(1),
(2), (4) Date: Jun. 15, 2010

(87) PCT Pub. No.: WO2009/077723
PCT Pub. Date: Jun. 25, 2009

(65) Prior Publication Data
US 2010/0261800 A1  Oct. 14, 2010

(30) Foreign Application Priority Data
Dec. 17, 2007  (EP) .................................... 07254902

(51) Int. Cl.
C07C 27/00 (2006.01)
C07C 67/36 (2006.01)
C07C 51/12 (2006.01)
C07C 27/20 (2006.01)

(52) U.S. Cl. ...................................... 518/700

(58) Field of Classification Search .................. 518/700; 560/232; 562/519; 568/909
See application file for complete search history.

(56) References Cited

FOREIGN PATENT DOCUMENTS

| EP | 0 056 488 | 7/1982 |
|---|---|---|
| EP | 0 109 645 | 5/1984 |
| GB | 2 162 172 | 1/1986 |
| WO | WO 83/03409 | 10/1983 |
| WO | WO 99/38836 | 8/1999 |

OTHER PUBLICATIONS

International Search Report for PCT/GB2008/004095, mailed Feb. 18, 2009.
Written Opinion of the International Searching Authority for PCT/GB2008/004095, mailed Feb. 18, 2009.

*Primary Examiner* — Jafar Parsa
(74) *Attorney, Agent, or Firm* — Nixon & Vanderhye

(57) ABSTRACT

Process for converting synthesis gas to ethanol, including the steps of 1) introducing synthesis gas, together with methyl ethanoate and/or ethyl ethanoate, into an alcohol synthesis unit to produce methanol and ethanol, 2) separating the methanol from the ethanol of step 1, 3) introducing methanol, from step 2, together with CO, into a carbonylation unit in the presence of a methanol carbonylation catalyst, to produce ethanoic acid, and 4) introducing ethanoic acid, from step 3, together with methanol and/or ethanol, into an esterification unit to produce methyl ethanoate and/or ethyl ethanoate. In step 5), methyl ethanoate and/or ethyl ethanoate, produced in step 4, are fed into the alcohol synthesis unit of step 1, and in step 6) ethanol from step 2 is recovered.

16 Claims, 1 Drawing Sheet

PROCESS FOR THE CONVERSION OF HYDROCARBONS INTO ETHANOL

This application is the U.S. national phase of International Application No. PCT/GB2008/004095 filed 12 Dec. 2008, which designated the U.S. and claims priority to EP Application No. 07254902.5 filed 17 Dec. 2007, the entire contents of each of which are hereby incorporated by reference.

The present invention relates to a process for the production of ethanol (and optionally methanol) from synthesis gas.

In particular the present invention relates to a process for the production of ethanol from a carbonaceous feedstock; wherein the carbonaceous feedstock is first converted to synthesis gas which is then converted to methanol, which is then converted to ethanoic acid, which is then esterified and which is then hydrogenated to produce ethanol in the same alcohol synthesis unit in which the said synthesis gas is converted to methanol.

BACKGROUND OF THE INVENTION

In recent years increased use and demand for alcohols such as methanol, ethanol and higher alcohols has led to a greater interest in processes relating to alcohol production. The said alcohols may be produced by the fermentation of, for example, sugars and/or cellulosic materials.

Alternatively alcohols, such as ethanol, may be produced from synthesis gas. Synthesis gas refers to a combination of $H_2$ and carbon oxides produced in a synthesis gas plant from a carbon source such as natural gas, petroleum liquids, biomass and other carbonaceous materials including coal, recycled plastics, municipal wastes; or any organic material. Thus, alcohol and alcohol derivatives may provide non-petroleum based routes for the production of valuable chemicals and fuels.

Generally, the production of alcohols, for example methanol, takes place via three process steps: synthesis gas preparation, methanol synthesis, and methanol purification. In the synthesis gas preparation step, an additional stage may be employed whereby the feedstock is treated, e.g. the feedstock is purified to remove sulphur and other potential catalyst poisons prior to being converted into synthesis gas. This treatment can also be conducted after synthesis gas preparation; for example, when coal or biomass is employed.

The reaction to produce alcohol(s) from synthesis gas is generally exothermic. The formation of $C_2$ and $C_{2+}$ alcohols is believed to proceed via the formation of methanol for modified methanol catalysts and cobalt molybdenum sulphide catalysts. However, the production of methanol is equilibrium-limited and thus requires high pressures in order to achieve viable yields. Hence, pressure can be used to increase the yield, as the reaction which produces methanol exhibits a decrease in volume, as disclosed in U.S. Pat. No. 3,326,956.

A low-pressure, copper-based methanol synthesis catalyst is commercially available from suppliers such as BASF, Johnson Matthey, and Haldor-Topsoe. Methanol yields from copper-based catalysts are generally over 99.5% of the converted $CO+CO_2$ present. Water is a by-product of the conversion of $CO_2$ to methanol and the conversion of CO synthesis gas to $C_2$ and $C_{2+}$ oxygenates. In the presence of an active water-gas shift catalyst, such as a methanol catalyst or a cobalt molybdenum catalyst the water equilibrates with the CO to give $CO_2$ and $H_2$. A paper entitled, "Selection of Technology for Large Methanol Plants," by Helge Holm-Larsen, presented at the 1994 World Methanol Conference, Nov. 30-Dec. 1, 1994, in Geneva, Switzerland, reviews the developments in methanol production and shows how further reduction in costs of methanol production will result in the construction of very large plants with capacities approaching 10,000 t per day.

Other processes for the production of $C_2$ and $C_{2+}$ alcohol(s), include the processes described hereinafter;

WO 8303409 describes a process whereby ethanol is produced by carbonylation of methanol by reaction with CO in the presence of a carbonylation catalyst to form ethanoic acid which is then converted to an ethanoate ester followed by hydrogenolysis of the ethanoate ester formed to give ethanol or a mixture of ethanol and another alcohol which can be separated by distillation. Carbonylation can be effected using a $CO/H_2$ mixture and hydrogenolysis can similarly be conducted in the presence of CO, leading to the possibility of circulating gas between the carbonylation and hydrogenolysis zones with synthesis gas, preferably a 2:1 $H_2$:CO molar mixture being used as make up gas.

U.S. Pat. No. 4,122,110 relates to a process for manufacturing alcohols, particularly linear saturated primary alcohols, by reacting CO with $H_2$ at a pressure between 2 and 25 MPa and a temperature between 150 and 400° C., in the presence of a catalyst, characterized in that the catalyst contains at least 4 essential elements: (a) copper (b) cobalt (c) at least one element M selected from chromium, iron, vanadium and manganese, and (d) at least one alkali metal.

U.S. Pat. No. 4,831,060 relates to the production of mixed alcohols from CO and $H_2$ gases using a catalyst, with optionally a co-catalyst, wherein the catalyst metals are molybdenum, tungsten or rhenium, and the co-catalyst metals are cobalt, nickel or iron. The catalyst is promoted with a Fischer-Tropsch promoter like an alkali or alkaline earth series metal or a smaller amount of thorium and is further treated by sulphiding. The composition of the mixed alcohols fraction can be selected by selecting the extent of intimate contact among the catalytic components.

Journal of Catalysis, 1988, 114, 90-99 discloses a mechanism of ethanol formation from synthesis gas over $CuO/ZnO/Al_2O_3$. The formation of ethanol from CO and $H_2$ over a CuO/ZnO methanol catalyst is studied in a fixed-bed microreactor by measuring the isotopic distribution of the carbon in the product ethanol when isotopically-enriched $^{13}C$ methanol was added to the feed.

As the importance of ethanol is ever increasing in today's world, so is the need and desire to produce ethanol from a carbonaceous feedstock with a higher carbon efficiency, a higher conversion and an improved productivity and selectivity. Hence, the present invention provides a process that allows one to produce ethanol from a carbonaceous feedstock, with an improved carbon efficiency, a higher selectivity and, in particular, with a more productive conversion to ethanol.

SUMMARY OF THE INVENTION

Figure 1:
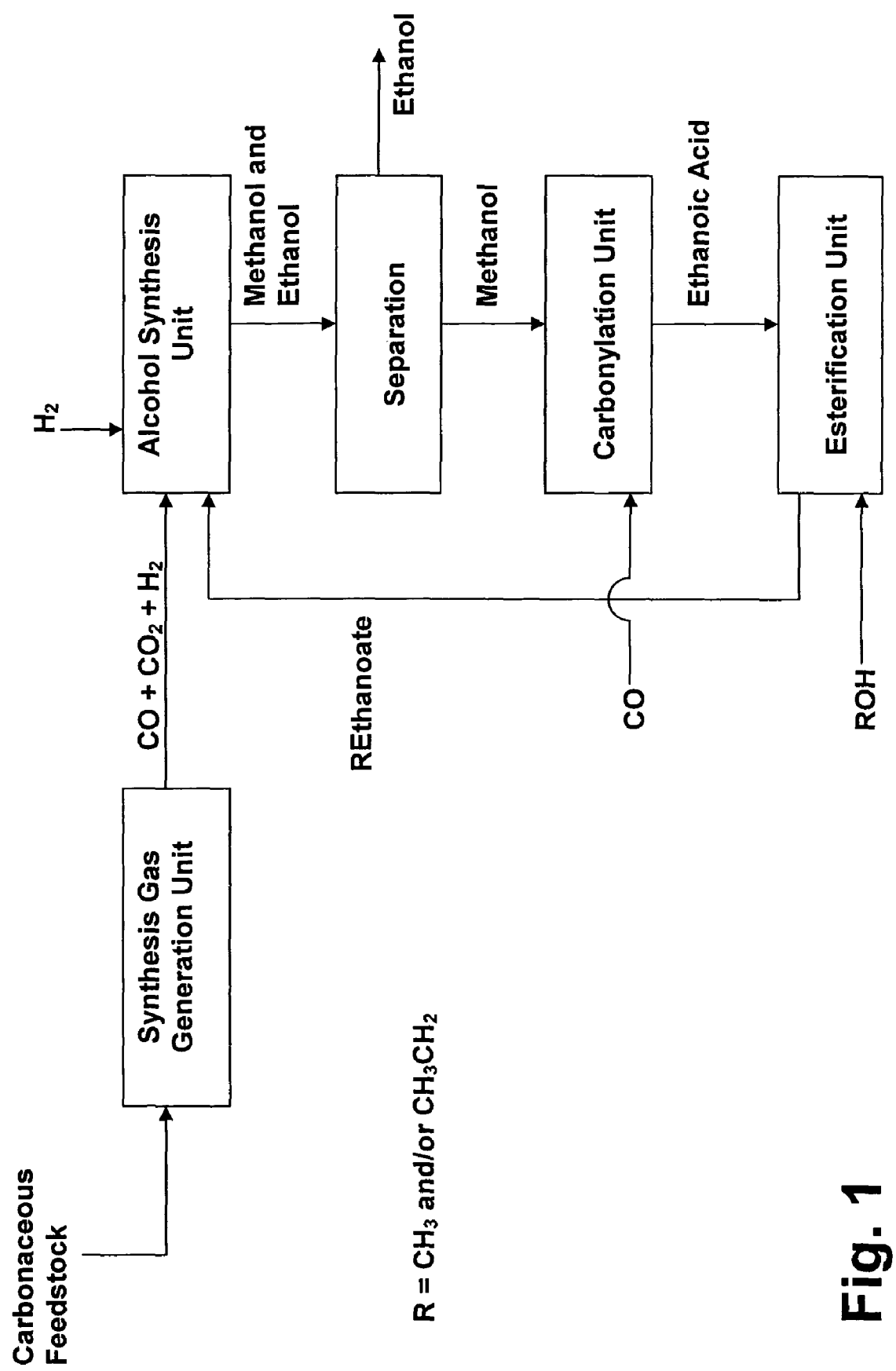
FIG. 1 represents an embodiment of a process scheme according to the present invention, wherein the references correspond to those used in the present description and appending claims.

Thus, the present invention relates to a process for the conversion of synthesis gas to ethanol, characterised by the following steps:
1) introducing synthesis gas, together with methyl ethanoate and/or ethyl ethanoate, into an alcohol synthesis unit to produce methanol and ethanol, 2) separating the methanol from the ethanol of step 1,
3) introducing methanol, from step 2, together with CO, into a carbonylation reactor in the presence of a methanol carbonylation catalyst, to produce ethanoic acid,
4) introducing ethanoic acid, from step 3, together with methanol and/or ethanol, into an esterification unit to produce methyl ethanoate and/or ethyl ethanoate,
5) feeding methyl ethanoate and/or ethyl ethanoate, produced in step 4, into the alcohol synthesis unit of step 1, and
6) recovering ethanol from step 2.

Furthermore, the present invention relates to a process for the conversion of a carbonaceous feedstock(s) into ethanol, wherein the carbonaceous feedstock is first converted into synthesis gas, which is subsequently converted into ethanol and characterised by the following steps:
1) introducing a carbonaceous feedstock into a synthesis gas reactor to produce a mixture of carbon oxide(s) and $H_2$,
2) introducing CO and $H_2$, from step 1, together with methyl ethanoate and/or ethyl ethanoate, into an alcohol synthesis unit to produce methanol and ethanol,
3) separating the methanol from the ethanol of step 2,
4) introducing methanol, from step 3, together with CO, into a carbonylation reactor in the presence of a methanol carbonylation catalyst, to produce ethanoic acid,
5) introducing ethanoic acid, from step 4, together with methanol and/or ethanol, into an esterification unit to produce methyl ethanoate and/or ethyl ethanoate,
6) feeding methyl ethanoate and/or ethyl ethanoate, produced in step 5, into the alcohol synthesis unit of step 2, and
7) recovering ethanol from step 3.

For the purposes of the present invention and appending claims the following terms are defined hereinafter:

The 'dew point temperature' is a threshold temperature, for example, for a given pure component or mixture of components, at a given pressure, if the system temperature is raised to above the dew point temperature, the mixture will exist as a dry gas. Likewise below the dew point temperature, the mixture will exist as a vapour containing some liquid.

'Gas' and/or 'gas phase' are defined as a pure component, or mixture of components, that are above the dew point temperature.

'Gas hourly space velocity' (GHSV) is defined as the volume of gas fed per unit volume of catalyst per hour, at standard temperature (0° C.) and pressure (0.101325 MPa).

'Liquid hourly space velocity' (LHSV) is defined as the volume of liquid fed per unit volume of catalyst per hour.

According to one aspect of the present invention, the synthesis gas feedstock, a mixture of carbon oxide(s) and $H_2$, that is used to produce the methanol feed stream, is preferably produced from a carbonaceous feedstock.

The carbonaceous feedstock is preferably a material such as biomass, plastic, naphtha, refinery bottoms, crude synthesis gas (from underground coal gasification or biomass gasification), smelter off gas, municipal waste, coal bed methane, coal, and/or natural gas, with coal and natural gas being the preferred sources. To one skilled in the art a combination of sources can also be used, for example coal and natural gas to advantageously increase the $H_2$ to carbon ratio.

Natural gas commonly contains a range of hydrocarbons (e.g. $C_1$-$C_3$ alkanes), in which methane predominates. In addition to this, natural gas will usually contain nitrogen, $CO_2$ and sulphur compounds. Preferably the nitrogen content of the feedstock is less than 40 mol %, more preferably less than 10 mol % and most preferably less than 2 mol %.

Processes for producing synthesis gas, in a synthesis gas plant, are well known. Each method has its advantages and disadvantages, and the choice of using a particular reforming process over another is governed by economic and available feed stream considerations, as well as by the desire to obtain the optimum $(H_2-CO_2):(CO+CO_2)$ molar ratio in the resulting synthesis gas that is suitable for further chemical processing. A discussion of the available synthesis gas production technologies is provided in both Hydrocarbon Processing, 1999, 78:4, 87-90, and 92-93 and Petrole et Techniques, 1998, 415, 86-93, and are both hereby incorporated by reference.

It is also known that the synthesis gas may be obtained by catalytic partial oxidation of hydrocarbonaceous material in a microstructured reactor as exemplified in IMRET 3: Proceedings of the Third International Conference on Microreaction Technology, ed. W. Ehrfeld, Springer Verlag, 1999, pages 187-196. Alternatively, the synthesis gas may be obtained by short contact time catalytic partial oxidation of hydrocarbonaceous feedstocks as described in EP 0303438. The synthesis gas can also be obtained via a 'compact reformer' process as described in Hydrocarbon Engineering, 2000, 5:5, 67-69; Hydrocarbon Processing, 2000, 79:9, 34; Today's Refinery, 2000, 15:8, 9; WO 9902254; and WO 0023689.

Typically, for commercial synthesis gas production the pressure at which the synthesis gas is produced from a steam reformer ranges from approximately 0.1 to 10 MPa, preferably 2 to 3 MPa and the temperatures at which the synthesis gas exits the reformer ranges from approximately 700 to 1000° C. Likewise, for commercial synthesis gas production the pressure at which the synthesis gas is produced from an auto-thermal reformer ranges from approximately 0.1 to 10 MPa, preferably 2 to 5 MPa and the temperatures at which the synthesis gas exits the reformer ranges from approximately 700 to 1300° C. Where the high temperatures are necessary in order to produce a favourable equilibrium for synthesis gas production, and to avoid metallurgy problems associated with carbon dusting. The synthesis gas contains a molar ratio of $(H_2-CO_2):(CO+CO_2)$ ranging from 0.8 to 3.0, which is dependent on the carbonaceous feedstock(s) and the method of reforming used. For example, when natural gas is used as the carbonaceous feedstock for steam reforming, the synthesis gas obtained usually has a maximum $(H_2-CO_2):(CO+CO_2)$ ratio of 3.0. However, when natural gas is used as the carbonaceous feedstock for auto-thermal reforming, the synthesis gas obtained usually has a $(H_2-CO_2):(CO+CO_2)$ ratio of 1.5.

According to a preferred embodiment of the present invention, the molar ratio, $(H_2-CO_2):(CO+CO_2)$, of the synthesis gas stream exiting the synthesis gas generation unit(s) is greater than 1.6, more preferably greater than 1.8 and most preferably greater than 2.0. Preferably, the molar ratio, $(H_2-CO_2):(CO+CO_2)$, of said synthesis gas stream exiting the synthesis gas generation unit(s) is less than 3.0, preferably less than 2.75, more preferably less than 2.4 and most preferably less than 2.2.

According to another embodiment of this invention when the carbonaceous feedstock used for synthesis gas generation is not an aliphatic hydrocarbon (e.g. coal, aromatic material, biomass) the molar ratio $(H_2-CO_2):(CO+CO_2)$ of the exit synthesis gas is preferably adjusted to the target value by addition of $H_2$ or removal of $CO_2$.

$CO_2$ may be removed by the use of a simple, yet effective, separation method known to those skilled in the art, for example, a "membrane separation method". Such membrane technologies can be found in 'Purification and Recovery Options for Gasification' D. J. Kubek, E. Polla, F. P. Wilcher, UOP, 1996.

Alternatively, $CO_2$ may be recovered and removed by any suitable method(s) known to those skilled in the art, for example, by reacting with amines; performing a methanol wash (i.e. the RECTISOL process) and/or by using hot potassium carbonate (e.g. the BENFIELD process).

According to a preferred embodiment of the present invention, the exit stream obtained from the synthesis gas reactor (e.g. using a steam reformer), comprises essentially a mixture of carbon oxide(s) and $H_2$. It can also comprise water, nitrogen and traces of unconverted hydrocarbons (e.g. $C_1$-$C_3$ alkanes).

According to a preferred embodiment of the present invention, during synthesis gas generation, an additional stage may be employed whereby the feedstock is first purified to remove sulphur and other potential catalyst poisons (such as halides or metals e.g. mercury) prior to being converted into synthesis gas; alternatively this treatment can also be performed after synthesis gas preparation for example, when coal or biomass are used.

According to the present invention, at least part of the said synthesis gas stream is then introduced into an alcohol synthesis unit, together with methyl and/or ethyl ethanoate (known herewith and hereinafter as the ethanoates), to produce a stream comprising methanol and ethanol, in addition to unreacted methyl ethanoate and ethyl ethanoate.

Additionally by-products such as methane and higher alcohols may also be produced during alcohol synthesis (i.e. methanol and ethanol synthesis). According to a preferred embodiment of this aspect of the present invention, the stream exiting the alcohol synthesis unit is subsequently purified to remove said by-products by any methods known to those in the art to obtain substantially pure methanol and ethanol products.

For the targeted production of ethanol the preferred molar ratio, $(H_2-CO_2):(CO+CO_2)$, (where the concentrations of relevant components are expressed in volume percent or mole percent), of the fresh synthesis gas feed stream fed into the alcohol synthesis unit is greater than 3.0, preferably greater than 3.8, more preferably greater than 4.0 and most preferably greater than 4.1. Preferably the molar ratio, $(H2-CO_2):(CO+CO_2)$, of the fresh synthesis gas feed stream fed into the alcohol synthesis unit is less than 8.5, preferably less than 6.0, more preferably less than 5.0 and most preferably less than 4.4. The Applicants have also unexpectedly found that the co-feed of CO and $CO_2$ into the alcohol synthesis unit was particularly beneficial to the selectivity of the process according to the present invention. Therefore $CO_2$ represents more than 1 vol %, preferably more than 2 vol % and most preferably more than 5 vol % of the total reactor gas phase composition.

In order to obtain the aformentioned high synthesis gas molar ratios, additional $H_2$ may need to be added to the synthesis gas feed stream exiting the synthesis gas generation unit. Preferably, the said $H_2$ is obtained from the aforementioned synthesis gas generation stage. This is preferably performed by first removing $CO_2$ and water from the generated synthesis gas followed by a cryogenic separation to isolate the substantially pure CO from the $H_2$. Alternative methods of separation, such as membrane separation technologies can also be employed. Alternatively, said $H_2$ stream may also be obtained from another suitable source, such as another chemical process (e.g. off-gas from steel manufacture or electrolysis). Said $H_2$ stream(s) may still contain inert impurities such as methane, nitrogen, noble gases, water and $C_1$ to $C_4$ paraffinic hydrocarbons, which are preferably removed before use.

An added advantage of the present invention, when compared to other processes in the field, is that the purification of the separated $H_2$ feed produced during synthesis gas generation has no requirement for the removal of carbon oxides. Indeed, this is advantageous when compared to a process with a separate hydrogenation stage for ethanoates where the carbon oxides act as poisons to the hydrogenation catalyst as well as increasing the formation of inert materials, thus necessitating an increased purge step.

According to a preferred embodiment of the present invention, the alcohol synthesis unit may be any reactor that is suitable for producing methanol and ethanol, for example a fluidised bed reactor or a fixed bed reactor, which can be run with or without external heat exchange equipments e.g. a multi-tubular reactor; or a fluidised bed reactor; or a void reactor.

Preferably the alcohol synthesis unit is operated at a temperature of more than 180° C., preferably more than 200° C. and most preferably more than 220° C.; and less than 290° C., preferably less than 280° C., more preferably less than 270° C. and most preferably less than 250° C. Preferably the alcohol synthesis unit is operated at pressure of more than 2 MPa and preferably more than 5 MPa; and less than 10 MPa and preferably less than 9 MPa. In fact, since methanol synthesis is an exothermic reaction, the chosen temperature of operation is governed by a balance of promoting the forward reaction (i.e. by not adversely affecting the equilibrium) and aiding the rate of conversion (i.e. higher productivity). The ethanol synthesis is also exothermic; however, in this case the chosen temperature of operation is governed by a balance of reaction rate and selectivity.

The GHSV for continuous operation may be in the range 50 to 50,000 $h^{-1}$, preferably from 1,000 to 30,000 $h^{-1}$, more preferably from 2,000 to 18,000 $h^{-1}$ and most preferably from 5,000 to 12,000 $h^{-1}$.

The ethanoates liquid substrate introduced into the alcohol synthesis unit preferably has an LHSV less than 10 $h^{-1}$, more preferably less than 5 $h^{-1}$ and most preferably less than 3 $h^{-1}$; for example, a typical LHSV for normal operation is approximately 1 $h^{-1}$.

A key feature of the present invention is that the synthesis of methanol from synthesis gas and the hydrogenation of ethanoate esters into their corresponding alcohols occur in the same alcohol synthesis unit. The catalyst for methanol synthesis from synthesis gas and the catalyst for ethanoate hydrogenation may be one and the same catalyst; or alternatively more than one catalyst may be employed in the alcohol synthesis unit. The catalyst, or catalysts, may be any catalyst known to those skilled in the art to catalyse the synthesis of methanol from synthesis gas and those known to those skilled in the art which have been reported to catalyse the hydrogenation of esters to alcohols.

For the avoidance of doubt, when it is hereinafter referred to as a mixture of a methanol catalyst and a hydrogenation catalyst, it also covers physical blends of the two catalysts and/or separate packed zones of the two catalysts in the same reactor(s); according to a preferred mode of operation, the hydrogenation catalyst is located downstream of said methanol synthesis catalyst; thus, according to a preferred embodiment of the present invention, the catalyst configuration of the alcohol synthesis unit is such that the stream comprising CO, $H_2$ and methyl ethanoate and/or ethyl ethanoate is first reacted in the presence of a methanol synthesis catalyst and subsequently reacted in the presence of a hydrogenation catalyst.

The preferred catalyst for the alcohol synthesis unit can be chosen amongst traditional methanol synthesis catalyst selected from one of the two following groups:
  the high pressure zinc catalysts, composed of zinc oxide and optionally a promoter; and
  ii. low pressure copper catalysts, composed of zinc oxide, copper oxide, and optionally a promoter.

A preferred methanol synthesis catalyst is a mixture of copper, zinc oxide, and a promoter such as chromia or alumina. The Applicants have unexpectedly found that the said methanol synthesis catalyst demonstrated high hydrogenation activities.

According to a preferred embodiment of the present invention, the preferred catalyst used in the alcohol synthesis unit is either a hydrogenation catalyst or consists of a mixture of the above methanol catalyst together with a hydrogenation catalyst. The hydrogenation catalyst can be selected from the following:
  (i) a precious metal based catalyst, comprising of at least one noble metal from Group VIII of the periodic table (CAS version, for example iron, ruthenium, osmium, cobalt, rhodium, iridium, nickel, palladium, platinum) and at least one of the metals chosen from rhenium, tungsten and/or molybdenum; and optionally an additional metal, that is capable of alloying with said Group VIII noble metal;
  (ii) a copper-based catalyst (for example a copper chromite or a mixed copper metal oxide based catalyst wherein the second metal can be copper, zinc, zirconium or manganese), and
  (iii) mixtures thereof.

According to a preferred embodiment of the present invention, the catalyst(s) used in the alcohol synthesis unit (which may be the aforementioned methanol catalyst and/or the aforementioned hydrogenation catalyst) is a copper based catalyst, most preferably comprising copper and zinc. This copper-based catalyst contains preferably more than 75 wt %, more preferably more than 90 wt % and most preferably more than 95 wt % of copper oxide and zinc oxide.

According to a preferred embodiment of the present invention, the hydrogenation catalyst (which may be mixed with the methanol catalyst) is a copper based catalyst which is a supported catalyst which comprises copper, and preferably promoters, such as cobalt and/or manganese and/or chromium.

All of the aforementioned hydrogenation catalysts may advantageously be supported on any suitable support known to those skilled in the art; non-limiting examples of such supports include carbon, silica, titania, clays, aluminas, zinc oxide, zirconia and mixed oxides. Preferably, the palladium based catalyst is supported on carbon. Preferably, the copper based catalyst is supported on zinc oxide.

According to the present invention, at least a part of the stream exiting the alcohol synthesis unit is passed through a separation unit (e.g. a separation column) to recover and collect a stream comprising the targeted ethanol and a stream comprising methanol.

This separation stage may be performed by any suitable means known to those skilled in the art, e.g. a sieve tray column, a packed column, a bubble cap column or a combination thereof.

Since unreacted methyl ethanoate and ethyl ethanoate can also be present in the exit stream from the alcohol synthesis unit, the Applicants have found the following preferred mode of operation(s):

(i) methanol/methyl ethanoate mixture can be easily recovered together with the methanol and fed directly into the downstream carbonylation unit, and/or
(ii) ethanol/ethyl ethanoate mixture can be advantageously recovered and recycled to the alcohol synthesis unit.

According to a preferred embodiment of the present invention, in order to minimize the cost of separation and recycle of methyl ethanoate and/or ethyl ethanoate within the process, the alcohol synthesis unit is operated at high conversion of ethanoate feed to ethanol such as greater than 75%, more preferably greater than 90% and most preferably greater than 95%.

Additionally by-products such as methane, ethane and other higher alcohols may also be produced during alcohol synthesis. According to a preferred embodiment of this aspect of the present invention, the streams exiting the separation zone are subsequently purified to remove said by-products from the methanol and ethanol streams by any methods known to those skilled in the art.

According to the present invention, at least a part of the aforementioned stream comprising methanol (and optionally methyl ethanoate), together with a substantially pure CO stream, are introduced into a carbonylation reactor. Preferably at least part, most preferably all, of the said methanol stream, emanates from the aforementioned alcohol synthesis unit. However in practice said methanol stream may also emanate from another suitable source, such as a bio-fermentation process and/or pyrolysis (e.g. wood pyrolysis).

Preferably at least a part of the said CO stream is obtained from the aforementioned synthesis gas generation stage. This is preferably performed by first removing $CO_2$ and water from the generated synthesis gas followed by a cryogenic separation to isolate the substantially pure CO from the $H_2$. A particular advantage according to the present invention is that both the $H_2$ fed to the alcohol synthesis unit and the CO fed to the carbonylation unit are obtained from the same synthesis gas separation stage. Alternative methods of separation, such as membrane separation technologies can also be employed. Alternatively, said CO stream may also be obtained from another suitable source, such as another chemical process (e.g. off-gas from steel manufacture).

Said substantially pure CO stream may contain inert impurities such as $CO_2$, methane, nitrogen, noble gases, water and $C_1$ to $C_4$ paraffinic hydrocarbons which are preferably removed before use.

According to this aspect of the present invention; the step of introducing methanol, together with CO, into a carbonylation reactor is performed under conditions favourable for producing ethanoic acid.

There are many examples in the prior art which disclose carbonylation processes that can be suitably used in the present invention.

For example, such carbonylation processes can be made in the presence of iridium catalysts as described in U.S. Pat. No. 3,772,380. UK patent GB 1276326 also describes the preparation of mono-carboxylic acids by carbonylation of alcohols in the presence of rhodium or iridium catalysts, halogen promoters and water or an alcohol, ether or ester.

Carbonylation processes in the presence of ruthenium and osmium catalysts can also be suitably used in the present invention. Thus, UK patents GB 1234641 and GB 1234642 describe a process for the production of an organic acid by carbonylation of an alcohol in the presence of a noble metal catalyst selected from iridium, platinum, palladium, osmium and ruthenium and their compounds and a promoter which is halogen or halogen compound. According to Jenner et al, Journal of Molecular Catalysis, 1987, 40, 71-82 ruthenium compounds are effective carbonylation catalysts for converting primary alcohols into acids at high CO pressures. Standard conditions of 45 MPa CO pressure were used in the reported experiments. For example, UK patent application GB 2029409 describes a process for the preparation of aliphatic carboxylic acids by reacting CO with alcohols at an elevated pressure of 3.4 MPa or greater in the presence of a ruthenium catalyst and halogen-containing promoter.

According to a preferred embodiment of this aspect of the present invention, the carbonylation process takes place in the presence of an iridium catalyst together with at least one promoter; indeed, such catalyst systems have proven to have beneficial effects on the rate of carbonylation of methanol. Said carbonylation process is thus preferably performed in the presence of at least a finite concentration of water with a catalyst system comprising:
(a) an iridium catalyst, (b) methyl iodide and (c) at least one promoter.

Thus, according to a preferred embodiment of this aspect of the present invention the process for the production of ethanoic acid by carbonylation of methanol comprises contacting methanol with CO, in the liquid reaction composition, in a carbonylation reactor wherein, the liquid reaction composition comprises:
(a) ethanoic acid, (b) an iridium catalyst, (c) methyl iodide, (d) water and (e) at least one promoter.

According to an embodiment of this aspect of the present invention, during the carbonylation process, water may be formed in situ in the liquid reaction composition. For example, water may be produced via by-product formation, generated during methane production. Water may also be generated during the esterification reaction between methanol reactant and ethanoic acid product. Water may also be introduced to the carbonylation reactor together with, or separately from, other components of the liquid reaction composition. Water may be separated from other components of reaction composition withdrawn from the reactor and may be recycled in controlled amounts to maintain a preferred concentration of water in the liquid reaction composition. Preferably, the concentration of water in the liquid reaction composition of the carbonylation reactor is in the range 0.1 to 15 wt %, more preferably 1 to 10 wt %, most preferably 1 to 6.5 wt %.

The iridium catalyst in the liquid reaction composition may comprise any iridium containing compound which is soluble in the liquid reaction composition. The iridium catalyst may be added to the liquid reaction composition for the carbonylation reaction in any suitable form which dissolves in the liquid reaction composition or is convertible to a soluble form. Examples of suitable iridium-containing compounds which may be added to the liquid reaction composition include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^- H^+$, $[Ir(CO)_2Br_2]^- H^+$, $[Ir(CO)_2I_4]^- H^+$, $[Ir(CH_3)I_3(CO)_2]^- H^+$, $Ir_4(CO)_{12}$, $IrCl_3.3H_2O$, $IrBr_3.3H_2O$, $Ir_4(CO)_{12}$, iridium metal, $Ir_2O_3$, $IrO_2$, $Ir(acac)(CO)_2$, $Ir(acac)_3$, iridium ethanoate, $[Ir_3O(OAc)_6(H_2O)_3][OAc]$, and hexachloroiridic acid $[H_2IrCl_6]$, preferably, chloride-free complexes of iridium such as ethanoates, oxalates and acetoacetates which are soluble in one or more of the carbonylation reaction components such as water, alcohol and/or carboxylic acid. Particularly preferred is green iridium ethanoate which may be used in an ethanoic acid or aqueous ethanoic acid solution.

Preferably, the iridium carbonylation catalyst concentration in the liquid reaction composition is in the range 100 to 6000 ppm by weight of iridium, more preferably 700 to 3000 ppm by weight of iridium.

In the process of the present invention at least one promoter is present in the reaction composition. Suitable promoters are preferably selected from the group consisting of ruthenium, osmium, rhenium, cadmium, mercury, zinc, gallium, indium and tungsten, and are more preferably selected from ruthenium and osmium and most preferably is ruthenium. Preferably, the promoter is present in an effective amount up to the limit of its solubility in the liquid reaction composition and/or any liquid process streams recycled to the carbonylation reactor from the ethanoic acid recovery stage. The promoter is suitably present in the liquid reaction composition at a molar ratio of promoter:iridium of [0.5 to 15]:1. As noted above, the beneficial effect of a promoter such as ruthenium has been found to be greatest at the water concentration which gives the maximum carbonylation rate at any defined methyl ethanoate and methyl iodide concentration. A suitable promoter concentration is 400 to 5000 ppm by weight.

The promoter may comprise any suitable promoter metal-containing compound which is soluble in the liquid reaction composition. The promoter may be added to the liquid reaction composition for the carbonylation reaction in any suitable form which dissolves in the liquid reaction composition or is convertible to soluble form.

Examples of suitable ruthenium-containing compounds which may be used as sources of promoter include ruthenium (III) chloride, ruthenium (III) chloride trihydrate, ruthenium (IV) chloride, ruthenium (III) bromide, ruthenium metal, ruthenium oxides, ruthenium (III) methanoate, $[Ru(CO)_3I_3]^- H^+$, $[Ru(CO)_2I_2]_n$, $[Ru(CO)_4I_2]$, $[Ru(CO)_3I_2]_2$, tetra(aceto)chlororuthenium(II,III), ruthenium (III) ethanoate, ruthenium (III) propanoate, ruthenium (III) butanoate, ruthenium pentacarbonyl, trirutheniumdodecacarbonyl and mixed ruthenium halocarbonyls such as dichlorotricarbonylruthenium (II) dimer, dibromotricarbonylruthenium (II) dimer, and other organoruthenium complexes such as tetrachlorobis(4-cymene)diruthenium(II), tetrachlorobis(benzene)diruthenium(II), dichloro(cycloocta-1,5-diene)ruthenium (II) polymer and tris(acetylacetonate)ruthenium (III).

Examples of suitable osmium-containing compounds which may be used as sources of promoter include osmium (III) chloride hydrate and anhydrous, osmium metal, osmium tetraoxide, triosmiumdodecacarbonyl, $[Os(CO)_4I_2]$, $[Os(CO)_3I_2]_2$, $[Os(CO)_3I_3]^- H^+$, pentachloro-mu-nitrodiosmium and mixed osmium halocarbonyls such as tricarbonyldichloroosmium (II) dimer and other organoosmium complexes.

Examples of suitable rhenium-containing compounds which may be used as sources of promoter include $Re_2(CO)_{10}$, $Re(CO)_5Cl$, $Re(CO)_5Br$, $Re(CO)_5I$, $ReCl_3.xH_2O$, $[Re(CO)_4I]_2$, $[Re(CO)_4I_2]^- H^+$, and $ReCl_5.yH_2O$.

Examples of suitable cadmium-containing compounds which may be used include $Cd(OAc)_2$, $CdI_2$, $CdBr_2$, $CdCl_2$, $Cd(OH)_2$, and cadmium acetylacetonate.

Examples of suitable mercury-containing compounds which may be used as sources of promoter include $Hg(OAc)_2$, $HgI_2$, $HgBr_2$, $HgCl_2$, $Hg_2I_2$, and $Hg_2Cl_2$.

Examples of suitable zinc-containing compounds which may be used as sources of promoter include $Zn(OAc)_2$, $Zn(OH)_2$, $ZnI_2$, $ZnBr_2$, $ZnCl_2$, and zinc acetylacetonate. Examples of suitable gallium-containing compounds which may be used as sources of promoter include gallium acetylacetonate, gallium ethanoate, $GaCl_3$, $GaBr_3$, $GaI_3$, $Ga_2Cl_4$ and $Ga(OH)_3$.

Examples of suitable indium-containing compounds which may be used as sources of promoter include indium acetylacetonate, indium ethanoate, $InCl_3$, $InBr_3$, $InI_3$, $InI$ and $In(OH)_3$.

Examples of suitable tungsten-containing compounds which may be used as sources of promoter include $W(CO)_6$, $WCl_4$, $WCl_6$, $WBr_5$, $WI_2$, or $C_9H_{12}W(CO)_3$ and any tungsten chloro-, bromo- or iodo-carbonyl compound.

Preferably, the iridium- and promoter-containing compounds are free of impurities which provide or generate in situ ionic iodides which may inhibit the reaction, for example, alkali or alkaline earth metal or other metal salts.

Ionic contaminants such as, for example, (a) corrosion metals, particularly nickel, iron and chromium and (b) phosphines or nitrogen containing compounds or ligands which may quaternise in situ; should be kept to a minimum in the liquid reaction composition as these will have an adverse effect on the reaction by generating $I^-$ in the liquid reaction composition which has an adverse effect on the reaction rate. Some corrosion metal contaminants such as for example molybdenum have been found to be less susceptible to the generation of $I^-$. Corrosion metals which have an adverse affect on the reaction rate may be minimised by using suitable corrosion-resistant materials of construction. Similarly, contaminants such as alkali metal iodides, for example lithium iodide, should be kept to a minimum. Corrosion metal and other ionic impurities may be reduced by the use of a suitable ion exchange resin bed to treat the reaction composition, or preferably a catalyst recycle stream. Such a process is described in U.S. Pat. No. 4,007,130. Preferably, ionic contaminants are kept below a concentration at which they would generate 500 ppm by weight of $I^-$, preferably less than 250 ppm by weight of $I^-$ in the liquid reaction composition.

Preferably, the concentration of methyl iodide in the liquid reaction composition is in the range 1 to 20 wt %, preferably 5 to 16 wt %.

The partial pressure of CO in the carbonylation reactor is suitably in the range 0.1 to 7 MPa preferably 0.1 to 3.5 MPa and most preferably 0.1 to 1.5 MPa.

The presence of $H_2$ in the CO feed and generated in situ by the water-gas shift reaction is preferably kept low as its presence may result in the formation of hydrogenation products. Thus, the molar ratio of $H_2$ to CO reactant is preferably less than 0.01:1, more preferably less than 0.005:1 and yet more preferably less than 0.003:1 and/or the partial pressure of $H_2$ in the carbonylation reactor is preferably less than 0.1 MPa, more preferably less than 0.05 MPa and yet more preferably less than 0.03 MPa.

The catalyst system used in the carbonylation process of the present invention has been found to be particularly beneficial at relatively low partial pressures of CO where the rate of reaction may be dependent upon the CO partial pressure. Under these conditions, it has been found that the catalyst system has the advantage of providing an increased rate of reaction over catalyst systems without the promoters of the present invention. This advantage allows for an increased rate of reaction under conditions when the CO partial pressure is relatively low, for example due to a low total pressure in the carbonylation reactor or due to high vapour pressure of components of the liquid reaction composition, e.g. at high methyl ethanoate concentration in the liquid reaction composition or due to a high concentration of inert gases (for example nitrogen and $CO_2$) in the carbonylation reactor. The catalyst system may also have advantages of increasing rate of carbonylation when the rate of reaction is reduced by the availability of CO in solution in the liquid reaction composition resulting from mass transfer limitations, for example due to poor agitation.

The pressure of the carbonylation reaction is suitably in the range 0.9 to 19.9 MPa, preferably 0.9 to 9.9 MPa, most preferably 1.4 to 4.9 MPa. The temperature of the carbonylation reaction is suitably in the range 100 to 300° C., preferably in the range 150 to 220° C.

Ethanoic acid may advantageously be used as a solvent for said carbonylation reaction.

The carbonylation process of the present invention may be performed as a batch or continuous process, preferably as a continuous process and may be performed in any suitable reactor, known to those skilled in the art.

The ethanoic acid product may be removed from the carbonylation reactor by withdrawing liquid reaction composition and separating the ethanoic acid product by one or more flash and/or fractional distillation stages from the other components of the liquid reaction composition such as iridium catalyst, ruthenium and/or osmium and/or indium promoter, methyl iodide, water and unconsumed reactants which may be recycled to the reactor to maintain their concentrations in the liquid reaction composition. The ethanoic acid product may also be removed as a vapour from the stream exiting the carbonylation reactor.

Although halide promoters and stabilizers, such as methyl iodide, improve the efficiency and productivity of carbonylation processes, the continued presence of halide compounds in the carbonylation reaction products is undesirable if the product is employed as a starting material in a subsequent process employing a halide-sensitive catalyst where poisoning effects may be cumulative and irreversible. In a preferred embodiment the ethanoic acid product is purified of halide compounds. This purification treatment can be achieved by any appropriate method known to those skilled in the art. For example halides can be removed from the liquid phase using silver salts either unsupported, or supported, on an ion-exchange resin or a zeolite as exemplified in U.S. Pat. No. 5,344,976 and references therein.

According to the present invention, an ethanoic acid stream is introduced into an esterification unit, together with an alcohol(s) stream, in order to produce a stream comprising methyl ethanoate and/or ethyl ethanoate.

According to a preferred embodiment of the present invention, at least a part, preferably all, of the said ethanoic acid feed stream originates from the aforementioned carbonylation reaction; however in practice, it may also originate from another suitable source, such as wood pyrolysis and/or as a by-product of a fermentation process to produce alcohol(s).

The alcohol(s) stream comprises methanol, ethanol or advantageously a mixture of methanol and ethanol wherein at least a part—preferably all—of the methanol and/or ethanol are produced during the aforementioned alcohol synthesis stage, but may also originate from another appropriate source, such as a bio-fermentation process and/or wood pyrolysis.

According to a preferred embodiment of the present invention, the molar ratio of alcohol(s) to ethanoic acid, introduced into the esterification reactor is 1; however molar ratios between 1.1 and 3, preferably between 1.1 and 2 may advantageously be used, as explained hereinafter.

The esterification reactor is preferably any reactor that is suitable for conducting an esterification reaction, for example using a close-coupled reactor and distillation column due to the reaction being equilibrium limited. The esterification reaction may also be conducted in a reactive distillation column.

The esterification of ethanoic acid by alcohol is a reaction which is known to be catalysed by strong inorganic acids such as hydrochloric or sulphuric acid. Such reactions have been described in many textbooks of organic chemistry, for example in chapter 10 of I. L. Finar, Organic Chemistry Vol I, Longmans, 1963.

The esterification of ethanoic acid together with alcohol(s) may be catalysed by any suitable acid catalysts (homogeneous and/or heterogeneous catalysts).

Examples of common commercial homogeneous catalysts include sulphonic acids, such as p-toluene sulphonic acid and alkyl sulphonic acids; where alkyl sulphonic acids may be represented by the formula $RSO_3H$ wherein R is a $C_1$ to $C_{12}$ substituted or unsubstituted aliphatic hydrocarbyl group and with the added proviso that the alkyl sulphonic acid has a de-sulphonation temperature in excess of 186° C. A preferred member of this class of sulphonic acids is methane sulphonic acid ($CH_3SO_3H$), as exemplified in EP 0158499, which has a de-sulphonation temperature in excess of 220° C.

However any sulphonic acid which has a de-sulphonation temperature greater or equal to that of p-toluene sulphonic acid is preferred as a catalyst. The de-sulphonation temperature of a sulphonic acid is defined as "the minimum temperature at which the reaction (de-sulphonation) occurs at a practical rate at atmospheric pressure" (see page 429 of E. E. Gilbert, Sulphonation and Related Reactions, Interscience, 1965). The de-sulphonation temperature of p-toluene sulphonic acid is 186° C. hence the sulphonic acids used in the present invention preferably have de-sulphonation temperatures in excess of this and preferably in excess of 190° C.

The sulphonic acid catalyst is added to the reaction mixture so as to comprise from 0.1 to 5 wt % of the reactor contents.

Alternatively, said esterification can also be catalysed by using tin-based catalysts, such as di-butyl tin oxide.

Heterogeneous esterification catalysts may be operated in the gas phase (e.g. acidic zeolites or heteropolyacids) or alternatively in the liquid phase (e.g. ion-exchange resins).

The esterification process described may be operated at atmospheric pressure but it is preferably operated at superatmospheric pressure between 0.11 and 0.8 MPa.

The temperature of esterification is preferably greater than 80° C. and more preferably is in the range of 125 to 185° C.

The process may be operated continuously or batchwise. A suitable method for carrying out the esterification continuously is described in EP 0009886.

The reaction mixture may also contain in addition to the catalyst between 0.1 and 1 wt % of a corrosion inhibitor to reduce corrosion of the vessel. A preferred corrosion inhibitor is copper as a salt for example copper ethanoate.

According to the present invention the stream exiting the esterification reactor comprises methyl and/or ethyl ethanoate, as well as unreacted ethanoic acid, ethanol and/or methanol, esterification catalyst and water. This stream may be continuously removed from the reactor by distillation whilst the reaction occurs. According to a preferred embodiment of the present invention, the stream exiting the esterification reactor is purified to remove said ethanoic acid, esterification catalyst and water, before its introduction into the alcohol synthesis unit. After purification and before introduction into the alcohol synthesis unit, the ethanoate stream contains preferably less than 5 ppm wt of esterification catalyst, more preferably less than 1 ppm wt, most preferably less than 0.1 ppm wt. After purification and before introduction into the alcohol synthesis unit, the ethanoate stream contains preferably less than 5 wt % of ethanoic acid, more preferably less than 1 wt %, even more preferably less than 0.1 wt % and most preferably less than 100 ppm by weight. Preferably, after purification and before introduction into the alcohol synthesis unit, the ethanoate stream contains less than 20 mol %, preferably less than 2 mol %, more preferably less than 0.2 mol % of water; and the alcohol synthesis unit is most preferably operated in the absence of water.

According to an alternative embodiment of the present invention, water represents between 0.5 and 20 mol %, more preferably between 0.5 and 15 mol % and most preferably between 1 and 5 mol % of the total liquid feed (ethanoate, alcohol and water) to the alcohol synthesis unit.

The applicants have unexpectedly found a preferred mode of operation whereby a methyl ethanoate/methanol mixture and/or an ethyl ethanoate/ethanol mixture can also advantageously be used together with the ethanoate as a feed to the alcohol synthesis unit; this is particularly advantageous because it considerably simplifies the purification process. The selective introduction of the ethyl ethanoate/ethanol mixture as a feed to the alcohol synthesis unit has been proven to be particularly beneficial.

The methyl and/or ethyl ethanoate fed into the alcohol synthesis unit is preferably purified of sulphur and halide compounds. This purification treatment can be achieved by any appropriate method known to those skilled in the art. For example, halides and iodides can be removed in the liquid phase using silver salts (either homogeneous or supported) on either an ion-exchange resin or a zeolite, or for the removal of sulphides the purification treatment may be performed in the vapour phase, by passing the vapour over a sacrificial bed of zinc oxide (or copper zinc oxides).

Furthermore, the ethanoate feed is preferably vaporized prior to contacting the alcohol synthesis catalyst by either, heating the ethanoate(s) in a separate vaporizer prior to having contact with the synthesis gas or, by heating the ethanoate(s) within the synthesis gas (e.g. either in a separate vessel or on a prebed to the alcohol synthesis reactor). The feed mixture including recycles entering the alcohol synthesis unit (e.g. the synthesis gas, together with the ethanoate(s)) is preferably more than 10° C., preferably more than 20° C. above its dew point temperature.

By recycling at least a part, preferably all, of the aforementioned stream(s) exiting the esterification unit into the alcohol synthesis reactor, the applicants were able to achieve a higher efficiency and an enhanced conversion towards ethanol.

It should be noted that whilst all of the aforementioned temperature and pressure operating conditions form preferred embodiments of the present invention, they are not, by any means, intended to be limiting, and the present invention hereby includes any other pressure and temperature operating conditions that achieve the same effect.

EXAMPLES

The Examples demonstrate that methanol was produced via hydrogenation of CO in the same reactor as ethanol was produced from hydrogenation of methyl ethanoate or ethyl ethanoate. The Examples demonstrate that enough methanol can be produced to balance the overall synthesis gas to ethanol via ethanoic acid process without the need for a separate methanol reactor (i.e. a ratio of methanol to converted ester of greater than 2 was demonstrated in the methyl ethanoate Examples; and a methanol to converted ester ratio of greater than 1 was demonstrated in the ethyl ethanoate Examples).

Catalyst

The Catalyst used in these Examples was T-2130 (supplied by Süd-Chemie), which has the following composition: CuO (33 wt. %), ZnO (66 wt. %).

Catalyst Testing

The catalyst testing experiments were carried out in a pressure flow reactor. The catalyst was heated to 100° C. under a flow of 5 mol % $H_2$ in $N_2$ at 2.5 MPa and a GHSV of 6000 $h^{-1}$. The concentration of $H_2$ was increased in stages to 10, 20, 40, 70 and 100 mol % with a 1 h dwell time at each stage. The catalyst was heated at 1° C./min to a holding temperature of 200° C. and was held for a dwell time of 1 h. At this point catalyst activation was considered complete.

EXAMPLE 1

A mixture of $H_2$ (70 vol %), CO (10 vol %), methyl ethanoate (4 vol %) and $N_2$ (16 vol %) was passed over T-2130 at 240° C., with a pressure of 7.6 MPa and a GHSV of 6837 $h^{-1}$ for 20 h; the LHSV was 1.0 $h^{-1}$. The observed conversion of methyl ethanoate was 96.7% and the selectivity to ethyl products (i.e. ethanol and the ethyl portion of ethyl ethanoate) was 97.9%. In this Example, methanol was produced from CO hydrogenation and methyl ethanoate hydrogenolysis. The ratio of methanol to converted methyl ethanoate was 2.24 (on a molar basis).

EXAMPLE 2

A mixture of $H_2$ (70 vol %), CO (10 vol %), methyl ethanoate (4 vol %) and $N_2$ (16 vol %) was passed over T-2130 at 250° C., with a pressure of 7.6 MPa and a GHSV of 6837 $h^{-1}$ for 20 h; the LHSV was 1.0 $h^{-1}$. The observed conversion of methyl ethanoate was 96.2% and the selectivity to ethyl products (i.e. ethanol and the ethyl portion of ethyl ethanoate) was 95.7%. In this Example, methanol was produced from CO hydrogenation and methyl ethanoate hydrogenolysis. The ratio of methanol to converted methyl ethanoate was 2.40 (on a molar basis).

EXAMPLE 3

A mixture of $H_2$ (70 vol %), CO (10 vol %), $CO_2$ (10 vol %), methyl ethanoate (4 vol %) and $N_2$ (6 vol %) was passed over T-2130 at 250° C., with a pressure of 7.6 MPa and a GHSV of 6837 $h^{-1}$ for 20 h; the LHSV was 1.0 $h^{-1}$. The observed conversion of methyl ethanoate was 95.1% and the selectivity to ethyl products (i.e. ethanol and the ethyl portion of ethyl ethanoate) was 98.6%. In this Example, methanol was produced from CO hydrogenation and methyl ethanoate hydrogenolysis. The ratio of methanol to converted methyl ethanoate was 3.11 (on a molar basis).

EXAMPLE 4

A mixture of $H_2$ (70 vol %), CO (10 vol %), ethyl ethanoate (4 vol %) and $N_2$ (16 vol %) was passed over T-2130 at 275° C., with a pressure of 7.6 MPa and a GHSV of 6837 $h^{-1}$ for 20 h; the LHSV was 1.2 $h^{-1}$. The observed conversion of ethyl ethanoate was 95.8% and the selectivity to ethanol was 89.7%. In this Example, methanol was produced from CO hydrogenation; the ratio of methanol to converted ethyl ethanoate was 1.33 (on a molar basis).

The invention claimed is:

1. Process for the conversion of synthesis gas to ethanol, comprising the following steps:
   1) introducing synthesis gas, together with methyl ethanoate and/or ethyl ethanoate, into an alcohol synthesis unit to produce methanol and ethanol,
   2) separating the methanol from the ethanol of step 1,
   3) introducing methanol, from step 2, together with CO, into a carbonylation unit in the presence of a methanol carbonylation catalyst, to produce ethanoic acid,
   4) introducing ethanoic acid, from step 3, together with methanol and/or ethanol, into an esterification unit to produce methyl ethanoate and/or ethyl ethanoate,
   5) feeding methyl ethanoate and/or ethyl ethanoate, produced in step 4, into the alcohol synthesis unit of step 1, and
   6) recovering ethanol from step 2.

2. Process for the conversion of a carbonaceous feedstock(s) into ethanol, wherein the carbonaceous feedstock is first converted into synthesis gas, which is subsequently converted into ethanol comprising the following steps:
   1) introducing a carbonaceous feedstock into a synthesis gas reactor to produce a mixture of carbon oxide(s) and $H_2$,
   2) introducing CO and $H_2$, from step 1, together with methyl ethanoate and/or ethyl ethanoate, into an alcohol synthesis unit to produce methanol and ethanol,
   3) separating the methanol from the ethanol of step 2,
   4) introducing methanol, from step 3, together with CO, into a carbonylation unit in the presence of a methanol carbonylation catalyst, to produce ethanoic acid,
   5) introducing ethanoic acid, from step 4, together with methanol and/or ethanol, into an esterification unit to produce methyl ethanoate and/or ethyl ethanoate,
   6) feeding methyl ethanoate and/or ethyl ethanoate, produced in step 5, into the alcohol synthesis unit of step 2, and
   7) recovering ethanol from step 3.

3. Process according to claim 1 wherein the alcohol synthesis unit is operated at a temperature of more than 180° C.

4. Process according to claim 1, wherein the alcohol synthesis unit is operated at a temperature of less than 290° C.

5. Process according to claim 1, wherein the alcohol synthesis unit is operated at a pressure of more than 2 MPa.

6. Process according to claim 1, wherein the alcohol synthesis unit is operated at a pressure of less than 10 MPa.

7. Process according to claim 1, wherein the alcohol synthesis unit is operated in the presence of one or more copper based catalyst(s).

8. Process according to claim 7, wherein the alcohol synthesis unit is operated in the presence of one or more catalysts comprising copper and zinc.

9. Process according to claim 1, wherein the alcohol synthesis unit is operated in the presence of a hydrogenation catalyst selected from
   (i) a precious metal based catalyst, comprising of at least one noble metal from Group VIII of the periodic table (CAS version) and at least one of the metals chosen from rhenium, tungsten and/or molybdenum; and optionally an additional metal, that is capable of alloying with said Group VIII noble metal,
   (ii) a copper-based catalyst, and
   (iii) mixtures thereof.

10. Process according to claim 1, wherein the stream exiting the alcohol synthesis unit comprises an ethanol/ethyl ethanoate mixture which is recovered and recycled to the alcohol synthesis unit.

11. Process according to claim 1, wherein the process for the production of ethanoic acid by carbonylation of methanol comprises contacting methanol with CO, in a liquid reaction composition, in a carbonylation unit, wherein the liquid reaction composition comprises:
   (a) ethanoic acid,
   (b) an iridium catalyst,
   (c) methyl iodide,
   (d) water and
   (e) at least one promoter.

12. Process according to claim 1, wherein the molar ratio of alcohol(s) to ethanoic acid, introduced into the esterification unit is comprised between 1.1 and 2.

13. Process according to claim 1, wherein the stream exiting the esterification unit is purified to remove ethanoic acid, carbonylation catalyst and water, before its introduction into the alcohol synthesis unit.

14. Process according to claim 1, wherein the methyl ethanoate and/or ethyl ethanoate stream is vaporized prior to its introduction into the alcohol synthesis unit.

15. Process according to claim 1, wherein the feed mixture including recycles entering the alcohol synthesis unit is more than 10° C. above its dew point temperature.

16. Process according to claim 15, wherein the feed mixture including recycles entering the alcohol synthesis unit is more than 20° C. above its dew point temperature.

* * * * *